(12) United States Patent
Lamraoui

(10) Patent No.: US 10,139,304 B2
(45) Date of Patent: *Nov. 27, 2018

(54) METHOD AND DEVICE FOR DETECTING A SLOW LEAK IN AN IMPLANTABLE HYDRAULIC OCCLUSION SYSTEM

(71) Applicant: UROMEMS, Grenoble (FR)

(72) Inventor: Hamid Lamraoui, Grenoble (FR)

(73) Assignee: UROMEMS, Grenoble (FR)

( * ) Notice: Subject to any disclaimer, the term of this patent is extended or adjusted under 35 U.S.C. 154(b) by 225 days.

This patent is subject to a terminal disclaimer.

(21) Appl. No.: 14/891,633

(22) PCT Filed: May 21, 2014

(86) PCT No.: PCT/EP2014/060468
§ 371 (c)(1),
(2) Date: Nov. 16, 2015

(87) PCT Pub. No.: WO2014/187871
PCT Pub. Date: Nov. 27, 2014

(65) Prior Publication Data
US 2016/0123835 A1    May 5, 2016

(30) Foreign Application Priority Data
May 21, 2013    (FR) .................................. 13 54538

(51) Int. Cl.
*A61B 5/00*    (2006.01)
*G01M 3/26*    (2006.01)
(Continued)

(52) U.S. Cl.
CPC .............. *G01M 3/26* (2013.01); *A61F 2/004* (2013.01); *A61F 5/003* (2013.01); *A61F 5/005* (2013.01);
(Continued)

(58) Field of Classification Search
CPC .... G01N 3/12; G01N 3/26; A61F 2/04; A61F 2/08; A61F 2/004; A61F 5/003;
(Continued)

(56) References Cited

U.S. PATENT DOCUMENTS 6,162,238 A    12/2000 Kaplan et al.
9,662,117 B2 *    5/2017 Forsell ................... A61B 17/12
(Continued)

FOREIGN PATENT DOCUMENTS

WO    WO-2009027196    3/2009

OTHER PUBLICATIONS

Hajivassiliou, C.A., "A Review of the Complication and results of Implantation of the AMS Artificial Urinary Sphincter", *European Urology*, vol. 35, (1999), 36-44.
(Continued)

*Primary Examiner* — Harshad R Patel
*Assistant Examiner* — Nigel Plumb
(74) *Attorney, Agent, or Firm* — Womble Bond Dickinson (US) LLP

(57) ABSTRACT

A detection method of a slow leak in a hydraulic occlusive system implantable in an animal or human body to occlude a natural conduit. The system includes a hydraulic circuit with an inflatable occlusive cuff containing a variable volume of fluid, surrounding a part of the natural conduit, a reservoir containing fluid, and a fluidic connection between the cuff and the reservoir. An activation device is coupled to a mobile element of the hydraulic circuit to transfer a determined volume of fluid from the reservoir to the cuff or from the cuff to the reservoir. A control unit urges the activation device to exert determined compression on the conduit. A variation of the compression exerted by the cuff on the conduit is created by transfer of an adjustable volume of said fluid between the reservoir and the cuff by measuring the evolution of the pressure in the hydraulic circuit.

10 Claims, 2 Drawing Sheets

(51) Int. Cl.
*A61F 2/00* (2006.01)
*A61F 5/00* (2006.01)

(52) U.S. Cl.
CPC . *A61F 2250/0003* (2013.01); *A61F 2250/008* (2013.01); *A61F 2250/0013* (2013.01)

(58) Field of Classification Search
CPC .............. A61F 5/005; A61F 2250/0003; A61F 2250/0013; A61F 2250/008; A61B 17/12009; A61B 5/4851
See application file for complete search history.

(56) References Cited

U.S. PATENT DOCUMENTS

| | | | | |
|---|---|---|---|---|
| 2010/0152532 A1* | 6/2010 | Marcotte | ................. | A61F 5/005 600/37 |
| 2010/0222802 A1* | 9/2010 | Gillespie, Jr. | ...... | A61B 17/0401 606/192 |
| 2011/0124955 A1 | 5/2011 | Ciquin et al. | | |
| 2012/0265456 A1* | 10/2012 | Snow | .................... | A61F 5/0056 702/51 |
| 2016/0113754 A1* | 4/2016 | Lamraoui | ............. | A61F 2/0036 623/14.13 |
| 2017/0325926 A1* | 11/2017 | Lamraoui | ............... | A61F 2/004 |

OTHER PUBLICATIONS

Lamraoui, Hamid, et al., "Development of a Novel Artificial Urinary Sphincter: A Versatile Automated Device", *IEEE/ASME Transactions on Mechatronics*, vol. 15, No. 6, (Dec. 2010), 916-924.

Maillet, Frederic, et al., "Management of Artificial Urinary Sphincter Dysfunction", *European Urology*, vol. 46, (2004), 241-246.

* cited by examiner

METHOD AND DEVICE FOR DETECTING A SLOW LEAK IN AN IMPLANTABLE HYDRAULIC OCCLUSION SYSTEM

FIELD OF THE INVENTION

The present invention relates to a method and device for detection of slow leaks in an implantable hydraulic occlusion system in an animal or human body to occlude a natural conduit.

This invention applies to any type of occlusion system, including urinary, anal, oesophageal or pyloric artificial sphincters or even gastric rings.

BACKGROUND OF THE INVENTION

The implantation of occlusive systems for fully or partially occluding a natural conduit of a patient is known for different indications.

For example, the treatment of urinary incontinence can involve implantation of an artificial sphincter in a patient.

Such a sphincter typically comprises an occlusive element placed around the urethra (in men or women) or sometimes the bladder neck (in women) or the prostate (in men) with the aim of exerting direct or indirect compression on the urethra to prevent urinary leaks, an activation device of said occlusive element to vary compression exerted on the urethra or the bladder neck, as well as a control unit of the activation device.

In the case of a hydraulic system, the occlusive element is an inflatable cuff containing a variable volume of fluid and the activation device comprises a reservoir containing fluid in fluidic connection with the cuff and an actuator for adding or removing said fluid to compress or decompress the cuff.

Such an artificial sphincter is described in particular in [1] and [2].

Another example of artificial sphincter is described in [3].

In such a system, it is possible that slow leaks occur in the hydraulic circuit.

«Slow leak» means in the present text a loss (respectively an addition) of liquid in a small quantity and stretching over a long period (at least several days, but more generally of the order of several months), causing a progressive drop (respectively a rise) in the pressure in the hydraulic circuit.

By opposition, a leak is considered as rapid if it causes a sharp decrease of pressure in the hydraulic circuit.

In this way, a rapid leak is detectable as soon as the triggering event has taken place (for example, disconnection of the tubing connecting the cuff to the fluid reservoir) or shortly after (for example, substantial damage of one of the materials ensuring sealing).

On the contrary, a slow leak becomes detectable only several days, or even several months after the occurrence of the breakdown which is the cause.

Such slow leaks can have different causes, including:
damage to a mechanical element of the hydraulic circuit, for example cracking of an element,
a defect of the connection of the tubing to the reservoir or to the occlusive cuff,
the porosity of the material constituting the tubing and/or the occlusive cuff (generally made of silicone) and inadequate concentration of the saline solution contained in the hydraulic circuit, generating a concentration gradient between the extracellular medium and the hydraulic circuit, which causes diffusion of water from the least concentrated medium to the most concentrated medium. In particular, if the fluid contained in the hydraulic circuit is insufficiently concentrated (hypotonic) relative to the external medium, the water will tend to diffuse to the exterior of the hydraulic circuit, leading to a decrease in the volume in said circuit; by contrast, if the fluid contained in the hydraulic circuit is too concentrated (hypertonic), there will be diffusion of water coming from the exterior to the hydraulic circuit, resulting in a rise in volume [4].

The effect of a slow leak is to alter the operation of the occlusive system.

In fact, for the same activation instruction, the fact that the hydraulic circuit contains less fluid or more than during implanting of the occlusive system results in a variation of the compression exerted on the conduit to be occluded.

In the case of where the slow leak leads to a loss of fluid, it can involve a decrease in the occlusion exerted by the cuff, and consequently a decrease in the efficacy of the occlusive system.

In the case of where the slow leak leads to an addition of fluid, it involves a progressive rise in pressure in the hydraulic circuit, causing excessive compression of the tissues surrounded by the cuff.

Occlusive systems proposed currently fail to detect a slow leak in the hydraulic circuit and to alert the patient or the practitioner thereof.

An aim of the invention is therefore to design a method and device for detecting this type of leak and, if needed, alert the practitioner or the patient.

BRIEF DESCRIPTION OF THE INVENTION

According to the invention, a method is proposed for detection of a slow leak in an implantable hydraulic occlusion system in an animal or human body to occlude a natural conduit, said occlusive system comprising:
  a hydraulic circuit comprising:
    an inflatable occlusive cuff containing a variable volume of fluid, surrounding a part of the natural conduit to be occluded,
    a reservoir containing fluid, and
    a fluidic connection between the cuff and the reservoir,
  an activation device coupled to a mobile element of said hydraulic circuit and adapted to move said mobile element to transfer a determined volume of fluid from the reservoir to the cuff or from the cuff to the reservoir, so as to vary the compression exerted by said cuff on said conduit,
  a control unit adapted to urge the activation device so as to exert determined compression on the conduit,
  the variation of the compression exerted by the cuff on the conduit being created by transfer of an adjustable volume of said fluid between the reservoir and the cuff.

Said detection method comprises:
  measuring the evolution of the pressure in the hydraulic circuit for a determined strain of the activation device, said determined strain being a position of the mobile element defining a determined volume of transferred fluid,
  detecting a slow leak in the hydraulic circuit when the pressure measured in said circuit for said determined strain of the activation device fulfils a predetermined criterion.

Within the scope of the present invention, a slow leak can involve any phenomenon of fluid transfer from or to the hydraulic circuit, using physical and/or chemical mechanisms, irrespective of whether direct flow, diffusion (especially of osmosis type), etc.

Also, such a leak can most often comprise transfer of fluid from the hydraulic circuit to the external medium, but in some cases also from the external medium to the hydraulic circuit.

According to an embodiment of the invention, said predetermined detection criterion can be selected from one of the following conditions, or a combination of said conditions:
- the pressure in the hydraulic circuit is less than a fixed value,
- the pressure in the hydraulic circuit is less than a percentage of a value of the pressure measured initially for said determined strain of the activation device, and
- a value obtained from a mathematical function constructed from a database of values of said pressure for said determined strain of the activation device, said pressure being recorded periodically over time, is less than a determined value.

In this case, a slow leak corresponding to a loss of fluid of the hydraulic circuit is detected.

According to an embodiment, the reservoir has a variable volume, the volume being adjusted by linear displacement of a mobile element moved by an actuator.

In this case, the determined strain of the activation device can be a stop position of the mobile element so as to maximise the volume of the reservoir.

According to an embodiment of the invention, the determined detection criterion is fulfilled when the pressure measured in the hydraulic circuit for said determined strain becomes less than a zero or negative threshold value.

According to another embodiment of the invention, to detect a slow leak leading to an addition of fluid into the hydraulic circuit, said predetermined detection criterion is selected from one of the following conditions or a combination of said conditions:
- the pressure in the hydraulic circuit is greater than a fixed value,
- the pressure in the hydraulic circuit is greater than a percentage of a value of the pressure measured initially for said determined strain of the activation device, and
- a value obtained from a mathematical function constructed from a database of values of said pressure for said determined strain of the activation device, said pressure being recorded periodically over time, is greater than a determined value.

Particularly advantageously, the method also comprises sending an alarm to a user if the detection criterion of a slow leak is fulfilled.

According to an embodiment, the activation device comprises a peristaltic pump, the volume of fluid to be transferred being adjusted by angular displacement of the rotor of said pump.

According to a preferred though non-limiting application of the invention, the occlusive system is an artificial urinary sphincter.

Another object relates to a device for executing said method.

More precisely this is a device for detection of a slow leak in a hydraulic occlusive system implantable in an animal or human body to occlude a natural conduit, said occlusive system comprising:
- a hydraulic circuit comprising:
  - an inflatable occlusive cuff containing a variable volume of fluid, surrounding a part of the natural conduit to be occluded,
  - a reservoir containing fluid, and
  - a fluidic connection between the cuff and the reservoir,
- an activation device coupled to a mobile element of said hydraulic circuit and adapted to move said mobile element to transfer a determined volume of fluid from the reservoir to the cuff or from the cuff to the reservoir, so as to vary the compression exerted by said cuff on said conduit,
- a control unit adapted to urge the activation device so as to exert determined compression on the conduit.

According to the invention, said device for detection comprises:
- a sensor adapted to measure the pressure in the hydraulic circuit,
- a sensor adapted to measure strain applied to the activation device,
- a processing unit adapted to:
  - measure, from measuring data of said sensors, the evolution of the pressure in the hydraulic circuit for a determined strain of the activation device, said determined strain being a position of the mobile element defining a determined volume of transferred fluid,
  - detect a slow leak in the hydraulic circuit when the pressure measured in said circuit for said determined strain of the activation device fulfils a determined criterion.

Finally, the invention relates to a hydraulic occlusive system implantable in an animal or human body to occlude a natural conduit, comprising a device adapted to execute the method for detection of a slow leak such as described hereinabove.

BRIEF DESCRIPTION OF THE DRAWINGS

Other characteristics and advantages of the invention will emerge from the following detailed description, in reference to the attached drawings, in which.

DETAILED DESCRIPTION OF THE INVENTION

In general, the occlusive system comprises an occlusive element surrounding a natural conduit to be occluded.

Depending on the application of the relevant occlusive system, the conduit to be occluded can be a urinary conduit (especially the urethra or the bladder neck), anal, oesophageal, pyloric conduit or even the stomach (case of gastric ring).

The occlusion of said conduit can be total (case of a urinary sphincter designed to prevent urinary leaks) or partial (case of a gastric ring designed to limit food entering the stomach).

The artificial sphincter also comprises an activation device for adjusting the compression exerted by the occlusive element.

There is therefore a link between the occlusive element and the activation device, which depends on the mode of action of said occlusive element.

In the case of an occlusive hydraulic system, the occlusive element is an inflatable cuff likely to contain an adjustable volume of fluid and the activation device comprises a fluid reservoir, the link between the cuff and the activation device comprising tubing for transferring fluid bidirectionally from the cuff to the reservoir depending on whether the aim is to increase or decrease the compression exerted.

In the oldest occlusive systems this activation device is controlled manually by the patient, for example by pressure exerted on a pump device arranged under the skin.

Currently, more refined systems are being developed to prevent the patient from exerting manual pressure on the pump for controlling the occlusive element.

The occlusive system comprises a control unit, also implantable in the body of the patient, adapted to control the activation device of the cuff.

There are currently different types of hydraulic occlusive systems, employing different technologies of activation.

These different occlusive systems are known to those skilled in the art.

As for artificial urinary sphincters, reference could be made for example to the following documents [1] to [3] cited above.

The activation device and the control unit are advantageously included in a casing implantable in the body of the patient designed to protect it.

The casing is typically made of biocompatible material.

Figure 1:
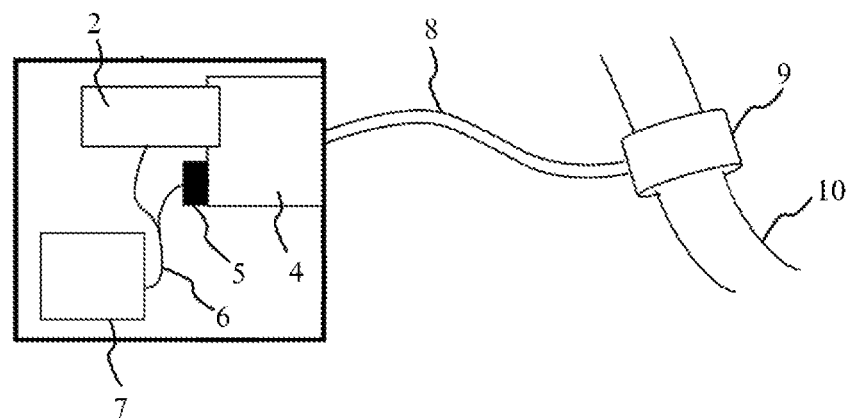
FIG. 1 is a block diagram of a hydraulic occlusive system according to an embodiment of the invention.

FIG. 1 is a block diagram of an occlusive hydraulic system associated with a leak detection device according to an embodiment of the invention.

The occlusive element 9 is in the form of an inflatable cuff likely to be filled with a variable quantity of fluid, with variation in fluid pressure inside the cuff varying compression exerted on the natural conduit 10 to be occluded.

A fluid reservoir 4, for example of saline solution, is arranged in fluidic connection with the cuff, by means of tubing 8.

The assembly of the cuff 9, the reservoir 4 and the tubing 2 forms the hydraulic circuit of the occlusive system.

This hydraulic circuit allows transferring some of the fluid from the reservoir to the cuff to increase compression exerted on the conduit 10 and inversely to transfer some of the fluid from the cuff to the reservoir to decrease compression exerted by the cuff on the conduit 10.

For this purpose, the occlusive system comprises also an activation device 2 coupled to the hydraulic circuit to perform this transfer of fluid and vary the compression exerted by the cuff on the conduit 10.

This fluid transfer involves displacement of a mobile element relative to a fixed element. According to the considered embodiment, this displacement can be translation or rotation.

According to an advantageous embodiment, the reservoir 4 has a variable volume.

For example, but non-limiting, the variation in volume can be achieved by moving a wall of the reservoir, the activation device 2 comprising an actuator for moving said wall.

In this way, the reservoir can comprise a rolling membrane, a piston, bellows or any other means for varying its volume by linear displacement of a mobile element relative to a fixed element forming the body of the reservoir.

Those skilled in the art can select from existing actuators an adequate actuator as a function of the planned implementation with respect to the reservoir.

A non-limiting example is a piezoelectric actuator, etc.

Even though it is not illustrated here, the activation device comprises a sensor for measuring the action exerted on the reservoir.

For example, if actuation consists of displacement of a mobile wall of the reservoir, said sensor can consist of a position sensor for determining the position of the mobile wall.

Calibrating determines both the relation between the position of the mobile wall and the variation in volume of the reservoir as well as the relation between the variation in volume of the reservoir and the pressure in the hydraulic circuit and finally between the pressure in the hydraulic circuit and the compression exerted on the conduit to be occluded.

The relation between the pressure in the hydraulic circuit and the volume transferred from the reservoir to the inflatable cuff can optionally be expressed in the form of a mathematical relation.

Depending on the case, this relation can be linear or not.

Therefore, it is possible to determine the displacement to be imposed on the mobile wall to obtain a given pressure of fluid in the hydraulic circuit in light of obtaining a given compression of the conduit 10.

In this case, displacement control of the activation device is based on measurement of the pressure in the hydraulic circuit.

For this reason, in the embodiment illustrated in FIG. 1, a pressure sensor 5 is arranged on a wall of the reservoir 4 so as to provide measurement of the fluid pressure in the reservoir.

The occlusive system comprises also a control unit 7 adapted to urge the activation device 2 so as to exert determined compression on the conduit 10.

The strain consists of an action which must be exerted by the activation device to obtain a determined compression of the conduit.

The link 6 between the control unit 7 and the activation device 2 has been illustrated in wired form in FIG. 1, but it is understood that it could be operated wireless, depending on the technology selected by those skilled in the art.

There is also a link 6 (wire or not) between the sensor 5 and the control unit 7.

Figure 2:
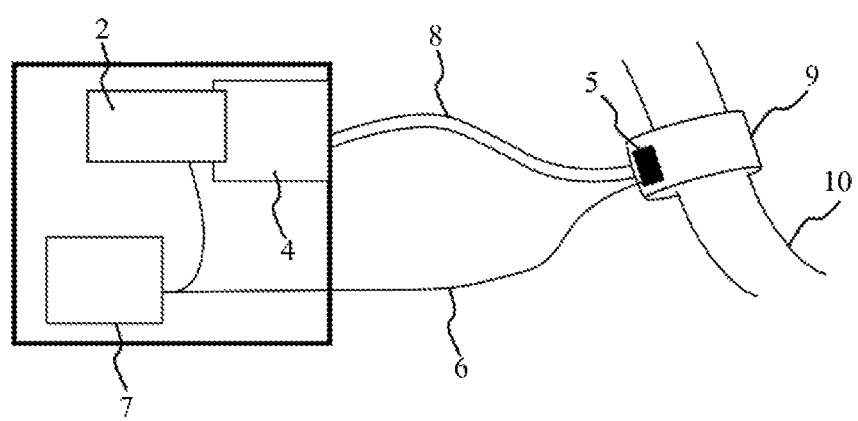
FIG. 2 is a block diagram of a hydraulic occlusive system according to another embodiment of the invention.

FIG. 2 illustrates another embodiment of a hydraulic occlusive system.

The components designated by the same reference signs as in FIG. 1 fulfil the same function and therefore will not be described in greater detail.

Relative to the device illustrated in FIG. 1, the sensor 5 for measuring the pressure in the hydraulic circuit is not arranged on a wall of the reservoir 4 but on the occlusive cuff 9, so as to directly measure the pressure on the conduit 10.

It is understood that a pressure sensor could be used in any other place of the hydraulic circuit or of the compression system without as such departing from the scope of the present invention.

In another embodiment (not illustrated), the activation device comprises a peristaltic pump for transferring fluid contained in the reservoir to the occlusive cuff and inversely. Such a pump typically has a fixed head containing deformable tubing, and a rotor mobile in rotation in the head, carrying rollers that deform and occlude the deformable tubing. The rotation of the rotor and rollers causes entrainment of the volume of fluid contained in the tubing between two adjacent rollers and enables the transfer of said volume of the reservoir to the cuff or inversely.

The embodiments described hereinabove are not intended to limit the invention and other activation means and other sensors could be selected without departing from the scope of the present invention.

Measuring the Pressure in the Hydraulic Circuit

Measuring the pressure in the hydraulic circuit can be done at any point of said circuit, for example with one or more of the pressure sensors mentioned above.

In the present invention, the focus is on evolution of the pressure in the hydraulic circuit in a particular situation, corresponding to a determined strain of the activation device.

This determined strain depends on the type of activation device used in the occlusive system.

To the extent where the transfer of fluid involves displacement (in translation or rotation) of a mobile element, the strain is advantageously a position of said element.

For example, when the reservoir comprises a mobile wall for varying its volume and the activation device is adapted to move said wall by a determined distance, the determined strain in which the pressure in the hydraulic circuit is monitored can correspond to the position of the wall defining a determined volume of fluid in the reservoir.

According to a preferred embodiment, an open stop position of said wall (corresponding to a maximal volume of the reservoir, the occlusive cuff being empty) is selected for said position.

When a slow leak occurs in the hydraulic circuit, the pressure in the hydraulic circuit for this determined position of the wall tends to decrease, and can even become negative.

Similarly, in the case where the activation device comprises a peristaltic pump, the strain for which the evolution of the pressure in the hydraulic circuit is monitored can be defined for an angular reference position of the rotor relative to the head of said pump to obtain given compression of the conduit or for maximising the volume of the reservoir linked to the peristaltic pump.

Monitoring of Pressure Over Time

To detect a possible slow leak in the hydraulic circuit, the pressure in the hydraulic circuit for the strain predetermined described hereinabove is recorded periodically.

The periodicity of measurement is not necessarily regular, that is, time intervals of different lengths can span between two consecutive measurements.

Also, recording of the pressure is not necessarily done each time the predetermined strain is encountered, but can optionally be done less often, according to a frequency determined by the practitioner.

Also, the periodicity of measurement can depend on the type of occlusive system in question.

For example, for a urinary or anal occlusive system, at least once per day there is opening of the occlusive cuff to allow for urination or defecation.

Consequently, for these systems, the pressure in the hydraulic circuit can be monitored daily, by recording the pressure in the hydraulic circuit during at least one urination or defecation.

In other systems (for example gastric rings), the system can be calibrated either during control performed by the user or autonomously by placing the activation device in a reference position, in conditions which do not affect the function of the occlusive system.

Criterion for Detecting a Slow Leak

The detection criterion of a slow leak can be selected from different possibilities, some of which will be described hereinbelow.

The focus is initially on the case where the slow leak leads to a loss of fluid of the hydraulic circuit.

According to a first embodiment of the invention, the detection criterion of such a slow leak is fulfilled when the pressure in the hydraulic circuit becomes less than a fixed value, independent of the patient, fixed arbitrarily.

This threshold value is preferably zero or negative.

According to another embodiment, the detection criterion of a slow leak is fulfilled when the pressure in the hydraulic circuit becomes less than a percentage of the value of the pressure measured initially.

For example, the value of the pressure in the hydraulic circuit is measured for a determined strain of the activation device after implantation of the occlusive system in the patient, and this value is selected as reference.

A percentage of this reference value is selected as being the value beyond which a slow leak is detected.

For example, this percentage could be of the order of 20%.

This value can be also negative and proportional to one or more parameters of the system.

An advantage of this criterion is that it considers the individual situation of the patient, since it is based on a measurement made on the patient on initialisation of the detection method.

According to another embodiment of the invention, the detection criterion of a slow leak involves the comparison not of the pressure measured itself, but of a function of said pressure, with a determined value.

In this way, this value to be compared to said determined value can be a value coming from a mathematical function constructed from a database of values of pressure measured periodically over time.

In this way, the presence of a slow leak can for example be considered when the product x.P drops below a threshold value, x being a parameter evolving over time to consider the ageing of materials of the occlusive system, and P the pressure measured in the hydraulic circuit for given strain.

For example, this threshold value can in particular be negative.

It is also feasible to define a more complex decision criterion which simultaneously takes into account different conditions by combining different criteria including those especially presented in the preceding paragraphs.

Advantageously, the choice of a zero or negative threshold value distinguishes a slow leak causing loss of fluid and atrophy of the natural conduit.

Atrophy is localised thinning of tissues compressed by the occlusive cuff.

Consequently, it results in a variation in the strain to be applied to the activation device to obtain a determined compression of the conduit.

However, in this case, the pressure in the hydraulic always stays positive for a determined strain of the activation device.

The observation of pressure less than a zero or negative threshold value in the hydraulic circuit for a determined strain of the activation device is therefore characteristic of a slow leak.

Figure 3:
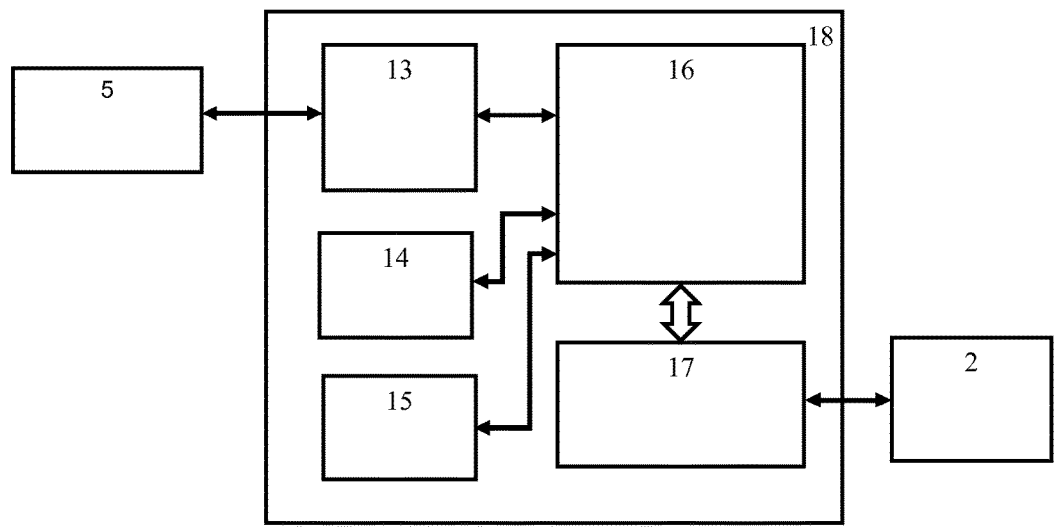
FIG. 3 is a block diagram of the architecture of the control unit of an occlusive system incorporating a device for detection of a slow leak.

FIG. 3 illustrates an embodiment of the general architecture of the processing unit for detection of a possible slow leak.

The processing unit 18 comprises a microprocessor 16 adapted to implement an algorithm for controlling a measurement of pressure when the predetermined strain of the activation device is observed, processing the measurement and compare the pressure measured to at least one detection criterion of a slow leak.

For this purpose, the microprocessor 16 communicates with at least one pressure sensor 5 by means of an interface 13.

Advantageously, the microprocessor communicates also with a sensor of the activation device, representative of the strain exerted on the activation device, to determine if the predetermined strain is applied.

Communication is sketched by arrows and can be achieved by a wired link or by a wireless link, according to known protocols.

The processing unit 18 also comprises a memory 14 in which are recorded the detection program, the measured pressure values, and the conditions to be fulfilled so that a slow leak is detected.

The processing unit also comprises one or more clocks 15.

The microprocessor 16 is connected to the interface 13, the memory 14 and the clock 15.

The microprocessor 16 communicates also with the activation device 2 by means of an interface 17.

Figure 4A:
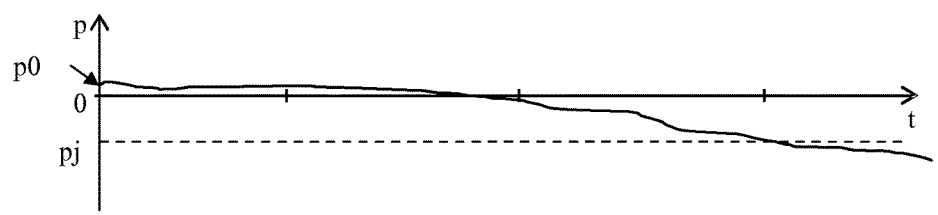
FIG. 4A illustrates an example of a curve of variation in pressure in the hydraulic circuit as a function of time in the case of a slow leak.
Figure 4B:
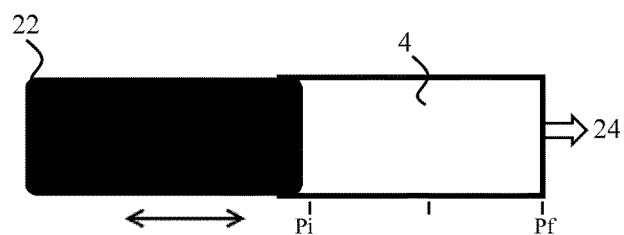
FIG. 4B shows the different positions of the piston in the case of a hydraulic occlusive system.

FIGS. 4A and 4B illustrate an example of detection of a slow leak in a hydraulic occlusive system.

In the embodiment shown in FIG. 4B, the reservoir 4 has a variable volume due of displacement of a piston 22.

The travel of the piston is defined by two positions limits: the position Pi, corresponding to an initial stop of the piston in which the occlusive cuff is empty, and the position Pf, corresponding to a final stop of the piston in which the occlusive cuff is filled with fluid so as to exert maximal compression of the conduit.

Arrow 24 indicates the output direction of the fluid from the reservoir to the occlusive cuff.

Focus is on the variation of pressure in the hydraulic circuit when the piston is in the position Pi.

The pressure in the hydraulic circuit on initialisation of the occlusive system is noted p0.

The graph of FIG. 4A shows the evolution of the pressure p over time when the piston is in the position Pi, in the case where a slow leak occurs.

As can be seen in this graph, the pressure p drops progressively from the initial value p0.

When the curve of the pressure p reaches a predetermined threshold noted pj, it is considered that a slow leak is detected.

If needed, an alert is sent by the processing unit to the attention of the patient and/or of the practitioner.

The practitioner can then decide to add a fresh volume of fluid to the hydraulic circuit, which avoids a fresh surgical procedure.

This addition can be made via an injection port which is generally provided on the hydraulic circuit, in particular on the reservoir.

The injection port can comprise a septum arranged in one of the walls of the reservoir which is placed opposite the skin of the patient, such that the practitioner can introduce a needle into the reservoir through the skin.

The septum is made of biocompatible material ensuring sealing of the reservoir while and after the needle is removed.

Silicone is generally employed for this usage.

Case where Fluid is Hypertonic

When the fluid is a hypertonic solution, there is a risk of diffusion of fluid from the exterior to the hydraulic circuit, likely to cause overpressurisation of the hydraulic circuit [4].

The invention detects such a situation and alerts a user.

In this case, the pressure for a position of the mobile element of the reservoir or of the peristaltic pump or a determined strain of the actuator will increase progressively.

The detection criterion can be selected from one of the criteria described hereinabove with the difference that detection is performed when the pressure is greater than a determined value.

When the curve of the pressure reaches the predetermined threshold, it is considered that cancellation is detected.

If needed, an alert is sent by the processing unit to the attention of the patient and/or of the practitioner.

The practitioner can then decide to remove a volume of fluid in the hydraulic circuit, thereby avoiding excessive compression of the tissues.

This removal can be done via an injection port which is generally provided on the hydraulic circuit, in particular on the reservoir.

REFERENCES

[1] WO 2009/027196
[2] Development of a Novel Artificial Urinary Sphincter, H. Lamraoui et al, IEEE/ASME Transactions on Mechatronics, Vol. 15, No. 6, December 2010
[3] U.S. Pat. No. 6,162,238
[4] F. Maillet, J.-M. Buzelin, O. Bouchot, and G. Karam, "Management of artificial urinary sphincter dysfunction," European Urology, vol. 46, no. 2, pp. 241-246, August 2004
[5] C. Hajivassiliou, "A review of the complications and results of implantation of the AMS artificial urinary sphincter," European Urology, vol. 35, no. 1, pp. 36-44, 1999

The invention claimed is:

1. A method for detection of a slow leak in a hydraulic occlusive system implantable in an animal or human body to occlude a natural conduit, said occlusive system comprising:
  a hydraulic circuit comprising:
    an inflatable occlusive cuff containing a variable volume of fluid, surrounding a part of the natural conduit to be occluded,
    a reservoir containing fluid, and
    a fluidic connection between the cuff and the reservoir,
  an activation device coupled to a mobile element of said hydraulic circuit and adapted to move said mobile element to transfer a determined volume of fluid from the reservoir to the cuff or from the cuff to the reservoir, so as to vary the compression exerted by said cuff on said conduit,
  a control unit adapted to urge the activation device so as to exert determined compression on the conduit,
  variation of the compression exerted by the cuff on the conduit being created by transfer of an adjustable volume of said fluid between the reservoir and the cuff,
said method comprising:
  measuring the evolution of the pressure in the hydraulic circuit for a determined displacement parameter of the activation device, said determined displacement parameter being a position of the mobile element defining a determined volume of transferred fluid, detecting a slow leak in the hydraulic circuit when the pressure measured in said circuit for said determined displacement parameter of the activation device fulfils a predetermined criterion.

2. The method according to claim 1, wherein to detect a slow leak manifesting as a loss of fluid of the hydraulic circuit, said predetermined detection criterion is selected from one of the following conditions or a combination of said conditions:

the pressure in the hydraulic circuit is less than a fixed value, the pressure in the hydraulic circuit is less than a percentage of a value of the pressure measured initially for said determined displacement parameter of the activation device, and a value obtained from a mathematical function constructed from a database of values of the pressure in the hydraulic circuit for said determined displacement parameter of the activation device, said pressure being recorded periodically over time, is less than a determined value.

3. The method according to claim 1, wherein the reservoir has a variable volume, the volume being adjusted by linear displacement of a mobile element moved by an actuator.

4. The method according to claim 3, wherein the determined displacement parameter of the activation device is a stop position of the mobile element so as to maximize the volume of the reservoir.

5. The method according to claim 1, wherein the determined detection criterion is fulfilled when the pressure measured in the hydraulic circuit for said determined displacement parameter becomes less than a zero or negative threshold value.

6. The method according to claim 1, wherein to detect a slow leak resulting in an addition of fluid into the hydraulic circuit, said predetermined detection criterion is selected from one of the following conditions or a combination of said conditions:

the pressure in the hydraulic circuit is greater than a fixed value, the pressure in the hydraulic circuit is greater than a percentage of a value of the pressure measured initially for said determined displacement parameter of the activation device, and a value obtained from a mathematical function constructed from a database of values of said pressure for said determined displacement parameter of the activation device, said pressure being recorded periodically over time, is greater than a determined value.

7. The method according to claim 1, further comprising sending an alarm to a user if the detection criterion of a slow leak is fulfilled.

8. The method according to claim 1, wherein the activation device comprises a peristaltic pump, the volume of fluid to be transferred being adjusted by angular displacement of the rotor of said pump.

9. The method of claim 1, wherein the occlusive system is an artificial urinary sphincter.

10. A hydraulic occlusive system implantable in an animal or human body to occlude a natural conduit, comprising:

a hydraulic circuit comprising:

an inflatable occlusive cuff containing a variable volume of fluid, surrounding a part of the natural conduit to be occluded, a reservoir containing fluid, and a fluidic connection between the cuff and the reservoir, an activation device coupled to a mobile element of said hydraulic circuit and adapted to move said mobile element to transfer a determined volume of fluid from the reservoir to the cuff or from the cuff to the reservoir, so as to vary the compression exerted by said cuff on said conduit, a control unit adapted to urge the activation device so as to exert determined compression on the conduit, a pressure sensor adapted to measure the pressure in the hydraulic circuit, a displacement sensor adapted to measure a displacement parameter applied to the activation device, said determined displacement parameter being a position of the mobile element defining a determined volume of transferred fluid, a processing unit adapted to:

from measuring pressure and displacement data of said sensors, measure the evolution of the pressure in the hydraulic circuit for a determined displacement parameter of the activation device, detect a slow leak in the hydraulic circuit when the pressure measured in said circuit for said determined displacement parameter of the activation device fulfils a determined criterion.

* * * * *